(12) United States Patent
Ikarashi et al.

(10) Patent No.: US 10,229,808 B2
(45) Date of Patent: Mar. 12, 2019

(54) TRANSMISSION-TYPE TARGET FOR X-RAY GENERATING SOURCE, AND X-RAY GENERATOR AND RADIOGRAPHY SYSTEM INCLUDING TRANSMISSION-TYPE TARGET

(71) Applicant: CANON KABUSHIKI KAISHA, Tokyo (JP)

(72) Inventors: Yoichi Ikarashi, Fujisawa (JP); Shuji Yamada, Atsugi (JP); Tadayuki Yoshitake, Cambridge, MA (US); Takao Ogura, Yokohama (JP); Takeo Tsukamoto, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 340 days.

(21) Appl. No.: 14/795,712

(22) Filed: Jul. 9, 2015

(65) Prior Publication Data

US 2016/0020061 A1 Jan. 21, 2016

(30) Foreign Application Priority Data

Jul. 16, 2014 (JP) ................................. 2014-145922

(51) Int. Cl.
*H01J 35/08* (2006.01)
*G01N 23/083* (2018.01)
*H05G 1/06* (2006.01)

(52) U.S. Cl.
CPC ............ *H01J 35/08* (2013.01); *G01N 23/083* (2013.01); *H01J 2235/081* (2013.01); *H01J 2235/186* (2013.01); *H05G 1/06* (2013.01)

(58) Field of Classification Search
CPC .... H01J 35/32; H01J 2235/205; H01J 35/065; H01J 1/304; H01J 2201/304; H01J 2201/30457; H01J 2201/306; H01J 2235/062; H01J 2235/081; H01J 35/06; H01J 35/20; H01J 7/18; H01J 35/08; H01J 2235/087; H01J 2235/166; H01J 2235/186; H01J 35/16; H01J 2235/06; H01J 35/025; H01J 2235/1204; H01J 35/12;

(Continued)

(56) References Cited

U.S. PATENT DOCUMENTS 6,487,272 B1 * 11/2002 Kutsuzawa ............ H01J 35/08
378/129
6,850,598 B1   2/2005 Fryda et al.
(Continued)

FOREIGN PATENT DOCUMENTS

CN    103765547 A    4/2014
JP    2002-527335 A  8/2002
(Continued)

*Primary Examiner* — Irakli Kiknadze
(74) *Attorney, Agent, or Firm* — Canon USA Inc., IP Division

(57) ABSTRACT

A transmission-type target includes a target layer and a transmissive substrate. The target layer is configured to generate X-rays in response to irradiation of electrons. The transmissive substrate supports the target layer and is configured to allow the X-rays generated in the target layer to pass therethrough. The transmissive substrate includes polycrystalline diamond in which grain boundaries extend in a substrate thickness direction and a substrate plane direction. The grain boundaries define an electrical potential of the target layer.

40 Claims, 7 Drawing Sheets

(58) Field of Classification Search
CPC ........... H01J 2235/086; H01J 2235/084; H01J 35/10; H01J 2235/088; H01J 2235/083; H01J 35/105; H01J 35/108; H01J 2235/068; H01J 2235/1291; A61N 5/1001; A61N 5/1002; A61N 2005/1003; H05F 3/06; H05G 1/06; C23C 16/06; G01N 23/04; G01N 23/083; G21K 1/02; A61K 2800/413; A61K 2800/43; A61K 2800/614; A61K 2800/81; A61K 8/0241; A61K 8/04; A61K 8/19; A61K 8/30; G02B 1/02; G02B 5/0858; G02B 5/0891
USPC ........................................ 378/119, 143, 123
See application file for complete search history.

(56) References Cited

U.S. PATENT DOCUMENTS

| | | | | |
|---|---|---|---|---|
| 7,907,700 | B2* | 3/2011 | Inaba | H01J 35/06 378/122 |
| 2004/0076260 | A1* | 4/2004 | Charles, Jr. | H01J 35/08 378/124 |
| 2005/0276977 | A1* | 12/2005 | Blackhall Smith | B82Y 30/00 428/403 |
| 2010/0055464 | A1* | 3/2010 | Sung | B01J 21/18 428/408 |
| 2010/0111260 | A1 | 5/2010 | Motz et al. | |
| 2010/0218801 | A1* | 9/2010 | Sung | B82Y 30/00 136/244 |
| 2015/0162161 | A1* | 6/2015 | Yamada | H01J 35/08 378/62 |

FOREIGN PATENT DOCUMENTS

| | | |
|---|---|---|
| JP | 2004-511885 A | 4/2004 |
| JP | 2007-524974 A | 8/2007 |
| JP | 2008-293879 A | 12/2008 |
| JP | 2009-545840 A | 12/2009 |
| JP | 2013-051156 A | 3/2013 |
| JP | 2014-099349 A | 5/2014 |
| SU | 1653548 A3 * | 5/1991 |
| TW | 201209847 A | 3/2012 |

* cited by examiner

TRANSMISSION-TYPE TARGET FOR X-RAY GENERATING SOURCE, AND X-RAY GENERATOR AND RADIOGRAPHY SYSTEM INCLUDING TRANSMISSION-TYPE TARGET

BACKGROUND OF THE INVENTION

Field of the Invention

The present invention relates to X-ray generators that generate X-ray radiation and that are applicable to medical equipment, nondestructive inspection apparatuses, and other similar instruments.

Description of the Related Art

There is a need to generate X-rays with stability while suppressing fluctuations in the intensity of outputting the X-rays in an X-ray generator.

One of the major factors in determining the stability in the X-ray generator can be thermal durability of a target that is a source of X-ray radiation.

"X-ray generating efficiency" in a target in an X-ray generator that irradiates the target with electron beams and generates X-rays is on the order of 1%. That is, almost all of the energy input into the target is converted into heat. If "heat dissipation" of heat generated in the target is insufficient, the temperature of the target increases excessively. The excessive heat produces negative effects including melting, evaporating, or thermal stress of the target, and a decrease in the adhesion of the target to its support. Therefore, insufficient or ineffective heat dissipation limits the thermal durability of the target.

One of the publicly known methods for improving the "X-ray generating efficiency" in the target is the use of a transmission-type target. A transmission-type target includes a target layer having a thin film formed of a heavy metal and includes a base allowing X-rays to pass therethrough and supporting the target layer. Japanese Patent Application Publication No. JP 2009-545840 (also published as WO 2008/060671) discloses a transmission-type target of the rotating anode type in which the "X-ray generating efficiency" is equal to or greater than 1.5 times that of a known reflection-type target of the rotating anode type.

The use of diamond in a base that supports a target layer in a transmission-type target is publicly known as a method for facilitating "heat dissipation" from the target to the outside. U.S. Pat. No. 6,850,598 discloses in its specification the use of single crystal diamond or polycrystalline diamond as a transmission substrate that supports a target layer and that allows X-rays to pass therethrough. Diamond has high heat resistance and high thermal conductivity, and also has high X-ray transmittance, and thus it is a suitable material as a supporting base in a transmission-type target.

One publicly known method to obtain stable X-ray output is disposing a connection electrode or wax material between a target layer and an anode member and establishing electrical connection therebetween.

However, for the above-described configuration including the connection electrode, fluctuations in outputting X-rays or discharge may occur. Therefore, there is a need to improve the reliability of the electrical connection between the target layer and the anode member.

SUMMARY OF THE INVENTION

Embodiments of the present invention disclose a transmission-type target for an X-ray generating source, and an X-ray generator and radiography system including the transmission-type target that can stably output X-rays with high reliability. One aspect of the present invention is directed to a transmission-type target that can be used in an X-ray generating tube as the X-ray generating source.

According to a first aspect of the present invention, a transmission-type target includes a target layer and a transmissive substrate. The target layer is configured to generate X-rays in response to irradiation of electrons. The transmissive substrate supports the target layer and is configured to allow the X-rays generated in the target layer to pass therethrough. The transmissive substrate includes polycrystalline diamond in which grain boundaries extend in a substrate thickness direction and a substrate plane direction. The grain boundaries define an electrical potential of the target layer.

A transmission-type target according to a second aspect of the present invention includes a target layer and a transmissive substrate. The target layer is configured to generate X-rays in response to irradiation of electrons. The transmissive substrate supports the target layer and is configured to allow the X-rays generated in the target layer to pass therethrough. The transmissive substrate includes polycrystalline diamond in which grain boundaries extend in a substrate thickness direction and a substrate plane direction. The grain boundaries include sp2 bonding.

Further features of the present invention will become apparent from the following description of the exemplary embodiments with reference to the attached drawings.

DESCRIPTION OF THE EMBODIMENTS

Embodiments of the present invention are described below with reference to the drawings. The dimensions, materials, shapes, and relative arrangement of components described in the embodiments are exemplary and do not intend to limit the scope of the invention unless expressly indicated otherwise.

Figure 2A:
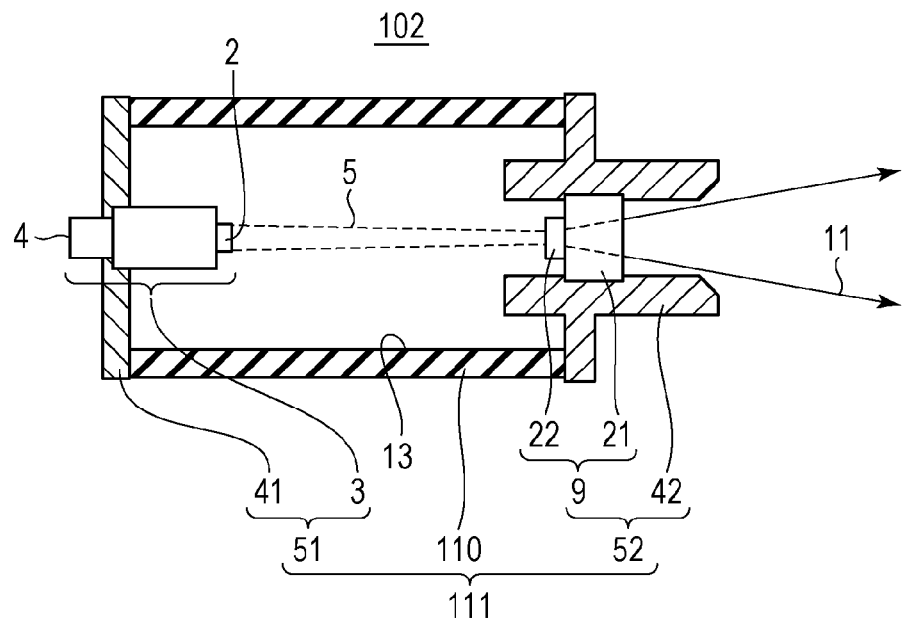
FIG. 2A is a schematic diagram that illustrates an embodiment of an X-ray generating tube that includes the transmission-type target according to the present invention.
Figure 2B:
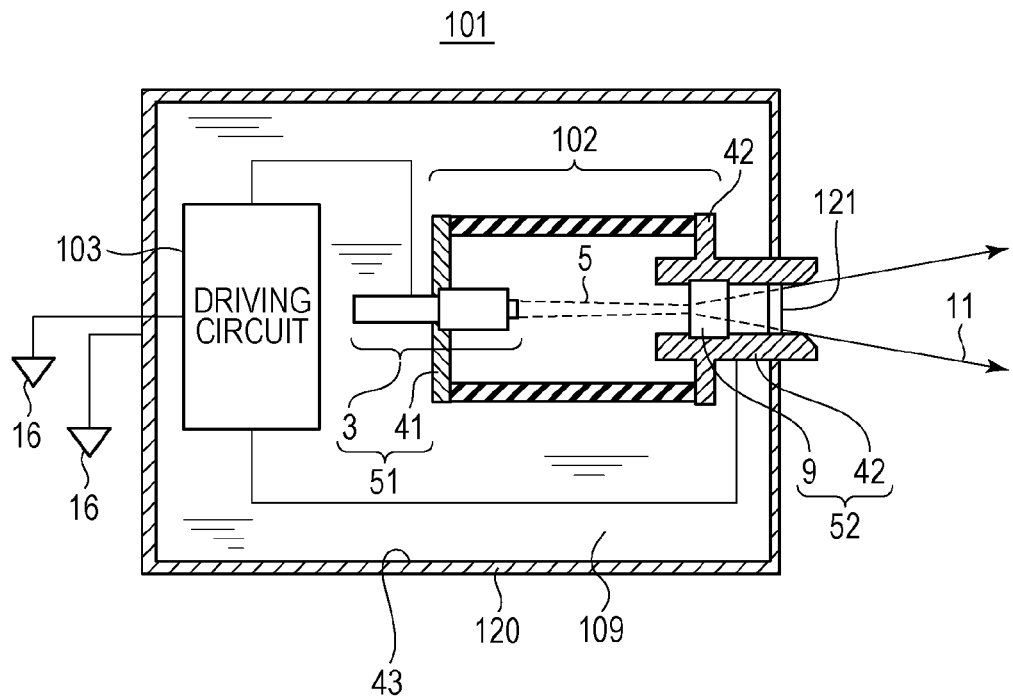
FIG. 2B is a schematic diagram that illustrates an embodiment of an X-ray generator that includes the X-ray generating tube with the transmission-type target.

First, an X-ray generating tube and X-ray generator in which a transmission-type target according to the present invention can be used are described. FIG. 2A is a diagram that illustrates an embodiment of an X-ray generating tube 102 including a transmission-type target 9 according to the present invention, and FIG. 2B illustrates an embodiment of an X-ray generator 101 including it. The transmission-type target 9 is referred to as target 9 in the specification below.

<X-Ray Generating Tube>

FIG. 2A illustrates the embodiment of the X-ray generating tube 102 of the transmission type including an electron emission source 3 and the target 9.

The X-ray generating tube 102 is configured to generate X-rays by irradiating a target layer 22 with an electron beam flux 5 emitted from an electron emitting portion 2 included in the electron emission source 3. Thus, the target layer 22 is arranged between the electron emission source 3 and a transmissive substrate 21, and the electron emitting portion 2 is arranged so as to be opposite the target layer 22.

The X-ray generating tube 102 is configured such that emission angle of X-rays generated in the target layer 22 is limited by a collimator having an aperture in front of the target 9 as needed and the X-rays are shaped into an X-ray flux 11, as illustrated in FIG. 2A. A tubular anode member 42 functions as the collimator. The anode member 42 retains the target 9 on its inner side.

Electrons contained in the electron beam flux 5 are accelerated to an incident energy required to generate X-rays in the target layer 22 by an accelerating electric field formed in an inner space 13 between a cathode 51 and an anode 52 in the X-ray generating tube 102.

The anode 52 includes at least the target 9 and the anode member 42 and functions as an electrode that defines an anode potential in the X-ray generating tube 102.

The anode member 42 is made of an electroconductive material and electrically connected to the target layer 22. The anode member 42 is a tubular member having a through hole, is connected to the transmissive substrate 21 such that the inner surface of the through hole and the periphery of the transmissive substrate 21 are connected to each other, as illustrated in FIG. 2A, and has the function of mechanically retaining the target 9. The anode member 42 contains heavy metal, such as tungsten or tantalum, and functions as a collimator by having the form including an extended portion having the aperture remaining on the front side of the target 9. The details of the embodiment of the target 9 are described later.

The inner space 13 in the X-ray generating tube 102 is vacuum in order to ensure a mean free path of the electron beam flux 5. The degree of vacuum of the inside of the X-ray generating tube 102 may preferably be between 1E-8 Pa and 1E-4 Pa, and in terms of the life of the electron emission source 3, may further preferably be between 1E-8 Pa and 1E-6 Pa. The electron emitting portion 2 and the target layer 22 are arranged in the inner space 13 or on the inner surface of an enclosure 111.

The inner space 13 in the X-ray generating tube 102 can be made vacuum by evacuation using an exhaust pipe and vacuum pump (not illustrated) and then sealing the exhaust pipe. A getter (not illustrated) may be arranged in the inner space 13 in the X-ray generating tube 102 in order to maintain the degree of vacuum.

The X-ray generating tube 102 includes an insulating tube 110 disposed in its trunk portion in order to achieve electrical insulation between the electron emission source 3, which is defined to a cathode potential, and the target layer 22, which is defined to an anode potential. The insulating tube 110 is made of an insulating material, such as a glass material or ceramic material. The insulating tube 110 may have a form having the function of defining the distance between the electron emitting portion 2 and the target layer 22, as illustrated in FIG. 2A.

The enclosure 111 may be made of a member that has a hermetic sealing property to maintain the degree of vacuum and that has robustness to have resistance to atmospheric pressure. The enclosure 111 is made up of the insulating tube 110, the cathode 51 including the electron emission source 3, and the anode 52 including the target 9. The cathode 51 and the anode 52 are connected to the respective opposite ends of the insulating tube 110 and constitute a portion of the enclosure 111. Similarly, it can be said that the transmissive substrate 21 acts as a transmission window through which X-rays generated in the target layer 22 is extracted to the outside of the X-ray generating tube 102 and constitutes a portion of the enclosure 111.

The electron emission source 3 is disposed so as to be opposite the target layer 22 included in the target 9. Examples of an element that can be used as the electron emission source 3 may include a hot cathode, such as an impregnated cathode, and a cold cathode, such as carbon nanotube. The electron emission source 3 can include a grid electrode or an electrostatic lens electrode (not illustrated) in order to control a beam diameter and an electron current density of the electron beam flux 5, on and off timings, and the like.

The cathode 51 includes an electroconductive cathode member 41 and the electron emission source 3. Because the cathode member 41 is a component member in the enclosure 111, a metal material having a coefficient of linear expansion near that of the insulating tube 110 is selected.

<X-Ray Generator>

FIG. 2B illustrates an embodiment of the X-ray generator 101 configured to extract the X-ray flux 11 toward the front of an X-ray transmission window 121. The X-ray generator 101 includes the X-ray generating tube 102 and a driving circuit 103 for driving the X-ray generating tube 102 inside a container 120 including the X-ray transmission window 121.

The driving circuit 103 applies a tube voltage between the cathode 51 and the anode 52, thus forming an accelerating electric field between the target layer 22 and the electron emitting portion 2. By appropriately setting a tube voltage Va in accordance with the layer thickness and the metal type of the target layer 22, a ray type required for imaging can be selected.

The container 120, which accommodates the X-ray generating tube 102 and the driving circuit 103, may have a sufficient strength as the container and good heat dissipation characteristics. Examples of a material used in the container 120 may include metal materials, including brass, iron, and stainless steel.

The container 120 has a remaining space 43 therein outside the X-ray generating tube 102 and the driving circuit 103. The remaining space 43 is filled with insulating liquid 109. The insulating liquid 109 is liquid having electrical insulating characteristics, serves to maintain the electrical insulating characteristics inside the container 120, and acts as a cooling medium for the X-ray generating tube 102. Examples of a material used as the insulating liquid 109 may include electrically insulating oils, including a mineral oil, a silicone oil, and a perfluoro oil.

<Radiography System>

Next, a configuration example of a radiography system 60 including the target 9 according to the present invention is described with reference to FIG. 3.

A system control unit 202 integrally controls the X-ray generator 101 and an X-ray detector 206. The driving circuit 103 outputs various kinds of control signals to the X-ray generating tube 102 under the control by the system control unit 202. The driving circuit 103 is accommodated in the container 120 included in the X-ray generator 101 together with the X-ray generating tube 102 in the present embodiment. Alternatively, the driving circuit 103 may be arranged outside the container 120. An emission state of the X-ray flux 11 emitted from the X-ray generator 101 is controlled based on the control signals output from the driving circuit 103.

The X-ray flux 11 emitted from the X-ray generator 101 is emitted to the outside of the X-ray generator 101 while its irradiation range is adjusted by a collimator (not illustrated) including a movable diaphragm. The emitted X-ray flux 11 passes through a subject 204 and is detected by the X-ray detector 206. The X-ray detector 206 converts the detected X ray into an image signal and outputs it to a signal processor 205.

The signal processor 205 performs predetermined signal processing on the image signal under the control by the system control unit 202 and outputs the processed image signal to the system control unit 202.

The system control unit 202 outputs a display signal for displaying an image on a display device 203 based on the processed image signal, to the display device 203.

The display device 203 displays the image based on the display signal on a screen as a photographed image of the subject 204.

The radiography system 60 can be used in nondestructive inspection of industrial products and in pathological diagnosis of human and animal bodies.

<Target>

Next, a basic embodiment of the target 9 being a feature of the present invention is described with reference to FIGS. 1A to 1C.

Figure 1A:
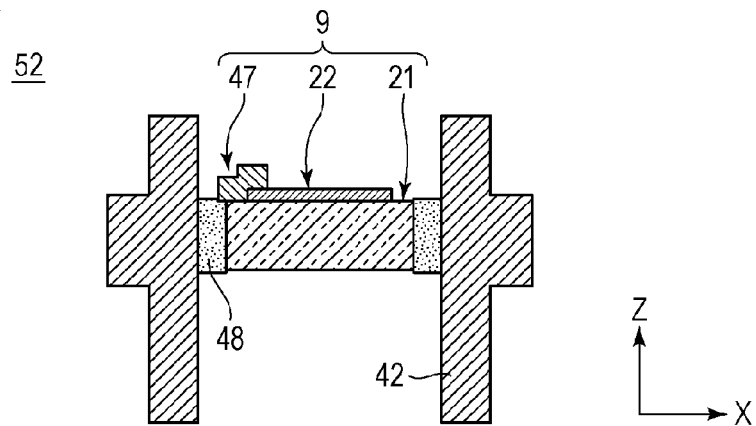
FIG. 1A is a cross-sectional view that describes an embodiment of an anode that includes a transmission-type target according to the present invention.

FIG. 1A illustrates the anode 52, which includes the target 9 retained by the tubular anode member 42. The target 9 has transmission-type arrangement including at least the target layer 22 containing a target metal and the transmissive substrate 21 supporting the target layer 22. The target 9 is subjected to electron irradiation in the target layer 22, allows X-rays to be extracted through the surface of the transmissive substrate 21 opposite the target layer 22, and operates. Accordingly, of the inner tubular portions in the anode member 42, one that faces the target layer 22 is an electron beam passage and another is a passage for use in extracting radiation. FIG. 1B is a plan view of the anode 52 illustrated in FIG. 1A seen from the side of the electron beam passage.

The transmissive substrate 21 is made of polycrystalline diamond in which a plurality of single crystal domains and grain boundaries are distributed in a substrate thickness direction and a substrate plane direction. A chemical vapor deposition (CVD) method, a solid-phase sintering method of baking microcrystal diamond, a liquid-phase sintering method of sintering a binder metal, such as cobalt, and microcrystal diamond by the action of dissolution and precipitation, or the like can be applied to the transmissive substrate 21, which is made of polycrystalline diamond. In terms of the ray quality of the X-rays and thermal conductivity, the CVD method may be used in that elements other than carbon are little and the thermal conductivity is high.

For the polycrystalline diamond obtained by the CVD method, a self-supported polycrystalline diamond layer can be formed by depositing polycrystalline diamond on a seed crystal substrate and then removing the seed crystal substrate. At least one of a mechanical removing method and a chemical removing method can be used in the removal of the seed crystal substrate.

The external shape of the transmissive substrate 21 is a flat form that includes a first surface supporting the target layer 22 and a second surface opposite the first surface, as illustrated in FIG. 1A. Examples of such an external shape may include a rectangular parallelepiped shape, a disk shape, and a truncated cone shape.

When the transmissive substrate 21 is disk-shaped, the target layer 22 capable of forming a necessary electron beam focal point can be disposed by setting the width, that is, diameter of the first surface at 2 mm to 10 mm. When the disk-shaped transmissive substrate 21 has a thickness of 0.3 mm to 3 mm, thermal transfer characteristics and X-ray transmittance in the substrate plane direction are obtainable. When a rectangular parallelepiped diamond base is used, the foregoing diameter range may apply to the length of a short side and the length of a long side of a surface included in the rectangular parallelepiped.

The target layer 22 contains a metal element having a high atomic number, a high melting point, and a high specific gravity as the target metal. The target metal is selected from among the metal elements at or above the atomic number 42. In terms of compatibility with the transmissive substrate 21, the target metal may be selected from the group of tantalum, molybdenum, and tungsten, which exhibit a negative standard free energy of forming metal carbide. The target metal may be contained in the target layer 22 as a pure metal having a single composition or an alloy composition, or may also be contained as a metal compound, such as a carbide, nitride, or oxynitride, of the above-described metals.

The layer thickness of the target layer 22 may be selected from the range of 1 μm to 12 μm. The lower and upper limits of the layer thickness of the target layer 22 are determined in terms of ensuring the intensity of outputting X-rays and reducing interface stress. The layer thickness may be in the range of 3 μm to 9 μm.

To form the portion of the anode 52 in the X-ray generating tube, the target 9 includes the anode member 42, a wax material 48, and a connection electrode 47 in the embodiment illustrated in FIG. 2A. The connection electrode 47 is an electroconductive member disposed to establish electrical connection between the target layer 22, which is isolated from the peripheral edge of the transmissive substrate 21, and the anode member 42. Examples of a material used in the connection electrode 47 may include metals, such as tin, silver, and copper, and metallic oxides. The firm thickness of the connection electrode 47 may be 100 nm or more in terms of electrical connection and may be 200 μm or less in terms of reducing separation resulting from membrane stress and reducing possibility of cracks.

The wax material 48 has the function of holding the target 9 on the anode member 42 and the function of electrically connecting the target layer 22 and the anode member 42. The wax material 48 is an alloy containing gold, silver, copper, tin, and/or other metals. By appropriately selecting the alloy composition in accordance with a joined member, adhesiveness between different materials of, for example, the transmissive substrate 21, connection electrode 47, anode member 42, and the like.

Next, a relationship between issues of the present invention and the transmissive substrate 21 is described in more detail with reference to FIGS. 7A to 7F.

FIGS. 7A to 7F illustrate anodes 252 to 254 as examples for reference. Each of the anodes 252 to 254 is extracted from the X-ray generating tube in which one of fluctuation in outputting X-rays, reduction in anode current, and occurrence of discharge is observed in an endurance accelerated test.

The anode 252 includes a target 209, a tubular anode member 242, and a wax material 248. The target 209 includes a transmissive substrate 221 made of polycrystalline diamond and a target layer 222. The target layer 222 is disposed up to the peripheral edge of the transmissive substrate 221 and is electrically connected to the anode member 242 with the wax material 248 disposed therebetween.

Figure 7A:
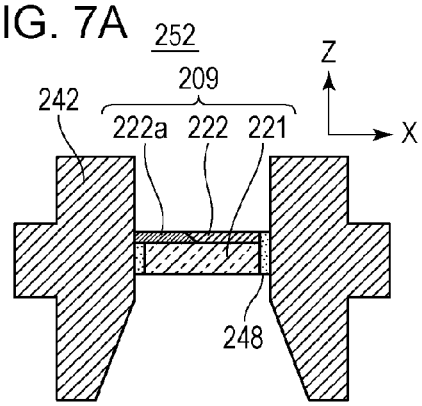
FIGS. 7A-7B, 7C-7D, and 7E-7F are respectively cross-sectional and plane-view diagram pairs that illustrate anodes including a transmission-type target in which hypothetical connection failure occurs between a target layer and an anode member due to a shape of an electrode member.
Figure 7B:
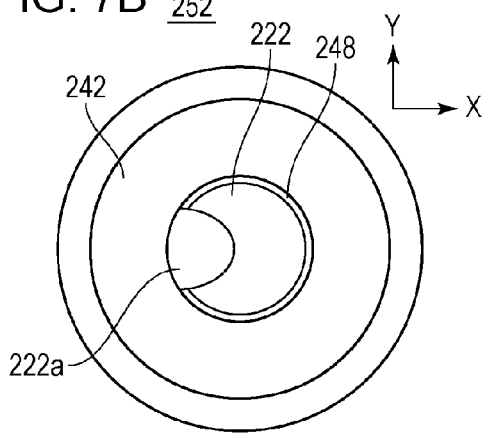

For an X-ray generating tube including the anode 252, fluctuations are observed in the intensity of outputting X-rays and in the ray quality after 530 exposing operations. The anode 252 extracted after 1,000 exposing operations in that X-ray generating tube is found to have a region 222a with changed composition in a part of the target layer 222, as illustrated in FIGS. 7A and 7B. The region 222a is identified as a region in which a contained metal component in the wax material 248 is diffused in the target layer 222. The observed fluctuations in the intensity of outputting X-rays and in the ray quality in the X-ray generating tube including the anode 252 are estimated to result from the region 222a, where the wax material 248 is diffused. The wax material 248 contains a component having high compatibility with the target layer 222 and has low thermal properties temperature, and thus its fluidity is high. The tendency of contaminating the target layer 222 is estimated to affect such diffusion.

The anode 253 includes the target 209, the tubular anode member 242, and the wax material 248. The target 209 includes the transmissive substrate 221 made of polycrystalline diamond, the target layer 222, and a connection electrode 247. The target layer 222 is disposed partially in a central area on a first surface of the transmissive substrate 221 and is electrically connected to the anode member 242 with the wax material 248 and the connection electrode 247 disposed therebetween. The connection electrode 247 in this reference example is configured such that it has a layer thickness larger than that of the target layer 222 in order to establish ohmic connection between the anode member 242 and the target layer 222.

Figure 7C:
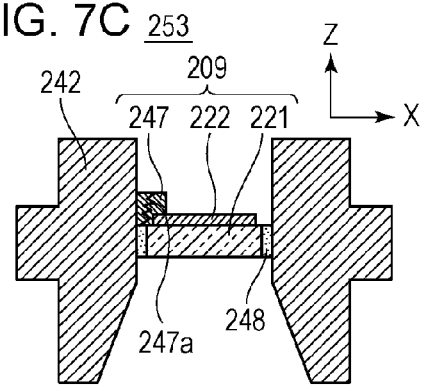
Figure 7D:
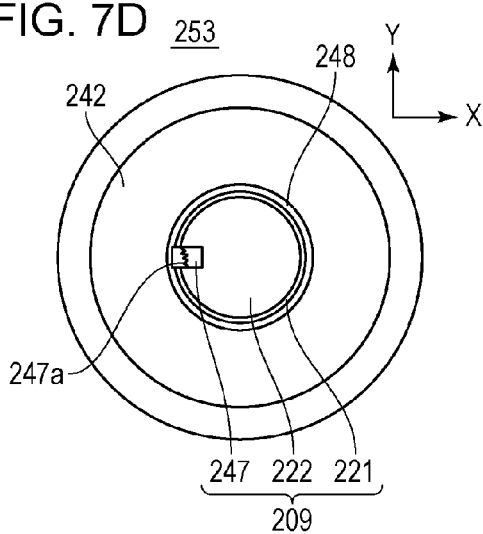

For an X-ray generating tube including the anode 253, fluctuations are observed in the intensity of outputting X-rays after 911 exposing operations. The anode 253 extracted after 1,000 exposing operations in that X-ray generating tube is found to have a crack 247a in the connection electrode 247, as illustrated in FIGS. 7C and 7D. The crack 247a is estimated to be stress rupture based on mismatching between a coefficient of linear expansion of the connection electrode 247 and that of the transmissive substrate 221. The fluctuations in outputting X-rays observed in the X-ray generating tube including the anode 253 are estimated to be caused by connection failure resulting from the crack 247a. That is, the crack 247a hampers stably defining the electrical potential of the target layer 222 in the anode 253 in this reference example.

The anode 254 is a transmission-type target that differs from the anode 253 in that a connection electrode 249 annularly overlaps the peripheral edge of the target layer 222.

Figure 7E:
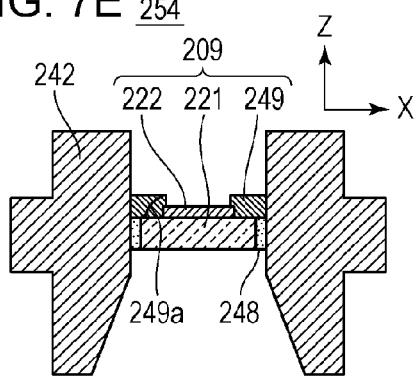
Figure 7F:
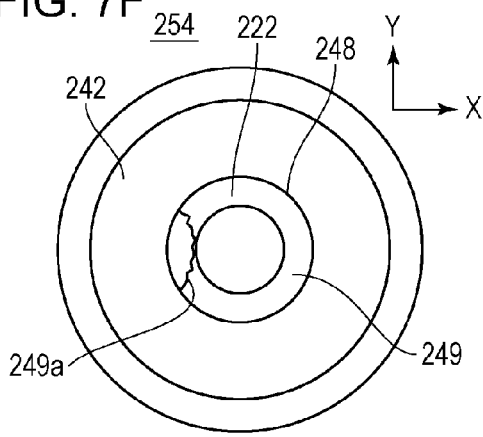

For an X-ray generating tube including the anode 254, fluctuations in the intensity of outputting X-rays and discharge are observed after 373 exposing operations. The observed discharge in the X-ray generating tube in this reference example is minute discharge in which, although the tube voltage can be applied sustainably, spike-like noise is superimposed on an anode current, and it has a strong correlation to the fluctuations in outputting X-rays. The anode 254 extracted after 1,000 exposing operations in that X-ray generating tube is found to have a crack 249a in the connection electrode 249, as illustrated in FIGS. 7E and 7F. The crack 249a is estimated to be stress rupture based on mismatching between a coefficient of linear expansion of the connection electrode 249 and that of the target layer 222. The fluctuations in outputting X-rays and the minute discharge observed in the X-ray generating tube including the anode 254 are estimated to be caused by connection failure resulting from the crack 249a. That is, the crack 249a hampers stably defining the electrical potential of the target layer 222 in the anode 254 in this reference example.

The details of the mechanism of instability relating to the outputting X-rays occurring in the X-ray generating tubes in the above-described reference examples are unclear. However, it is clear, at least, that there are cases where the electrical connection between the target layer 222 and the anode member 242 using the wax material 248, the connection electrode 247, or the connection electrode 249 alone is insufficient.

FIGS. 7B, 7D, and 7F are plan views of the anodes 252, 253, and 254 illustrated in FIGS. 7A, 7C, and 7E, respectively, seen from the Z direction.

In light of the above-described consideration of the inventors of the present invention, the transmission-type target of the present invention is characteristic in that the transmissive substrate includes polycrystalline diamond in which the grain boundaries extend in a substrate thickness direction and a substrate plane direction and the grain boundaries define the electrical potential of the target layer.

The transmission-type target having the characteristics of the present invention can exercise the function of stably defining the electrical potential of the target layer even if a crack occurs in the connection electrode and can improve reliability of the X-ray generating tube.

According to the present invention, because the transmissive substrate is a path for defining the electrical potential of the target layer, it is not necessary to have an increased layer thickness and increased forming range of the connection electrode. Thus, the advantage of reducing the possibility of occurrence of cracks in the connection electrode is obtainable.

Figure 1B:
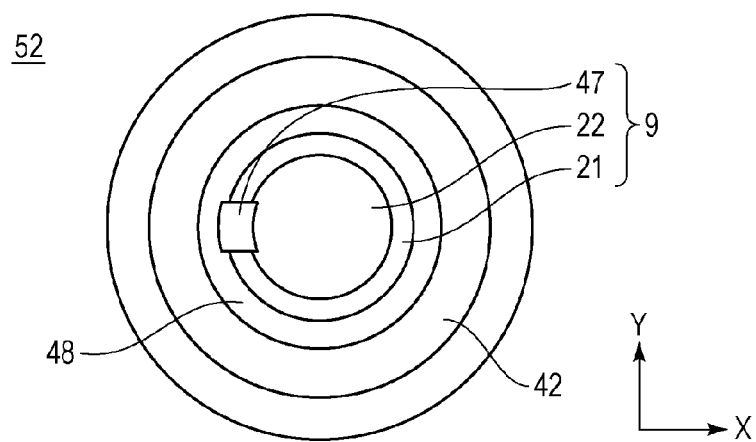
FIG. 1B is a plan view thereof.
Figure 1C:
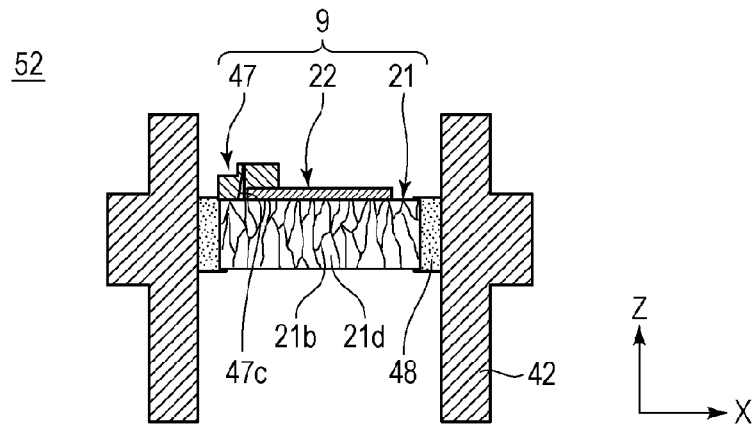
FIG. 1C is a cross-sectional view that illustrates an arrangement of grain boundaries in the transmissive substrate.

As illustrated in FIG. 1C, even in the target 9 in which a crack appears in the connection electrode 47, because the transmissive substrate 21 has a conducting path connected in parallel with respect to the connection electrode 47, the anode potential of the target layer 22 can be stably defined in a current field. When the target 9 in the present embodiment is applied to the X-ray generating tube, the occurrence of discharge and fluctuations in outputting X-rays are reduced.

Next, the transmissive substrate 21 in the target 9 applied to the present invention is described in further detail with reference to FIGS. 4A, 4B, 5A, and 5B.

Figure 4A:
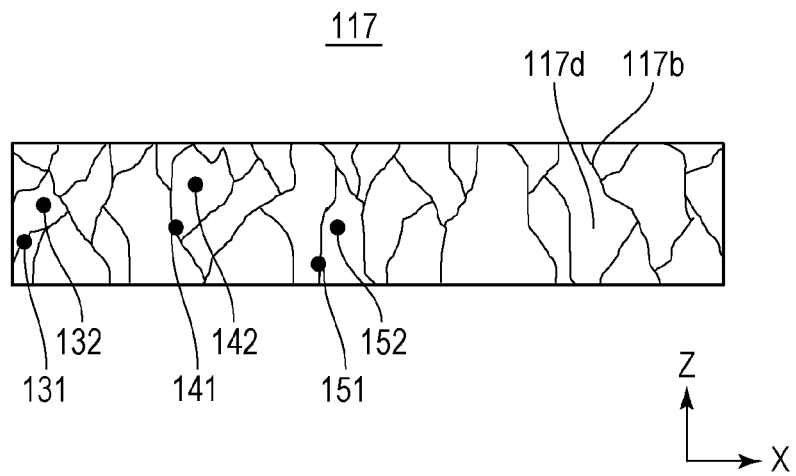
FIGS. 4A and 4B illustrate crystal grain distributions of polycrystalline diamond before and after graphitizing, respectively.

FIG. 4A schematically illustrates a polycrystalline image observed by an electron-beam backscattering diffraction method in a cross section of a polycrystalline diamond member 117 along the XZ plane. Grain boundaries 117b extend in the substrate thickness direction and the substrate plane direction, and a plurality of crystal grains 117d are present. The crystal grains 117d are single crystal domains with crystallographic orientation aligned inside.

For the crystal grains 117d, the sp3 bonding has long-range order as a domain of single crystal diamond, they easily convey phonon vibration and bear high thermal conductivity of the polycrystalline diamond member 117. In contrast, for the grain boundaries 117b, although they predominantly contain the sp3 bonding, the crystallinity is small, and thus the contribution to the thermal conductivity is smaller than that by the crystal grains 117d.

The crystal grains 117d are regions that contain carbon single bonds of the sp3 bonding and are electrically insulated. The grain boundaries 117b are boundary regions that relieve structural mismatching between neighboring crystal grains, and their crystallinity is small. Such structural mismatching includes crystallographic orientation mismatching. The grain boundaries 117b, which predominantly contain the sp3 bonding, are electrically insulated.

For a transmission-type target including the polycrystalline diamond member 117 as the transmissive substrate, if a crack occurs in the connection electrode 247 or 249, as illustrated in FIGS. 7C to 7F, because there is no current path for defining the electrical potential of the target layer 222, the fluctuations in outputting X-rays and an electric discharge occur.

Figure 4B:
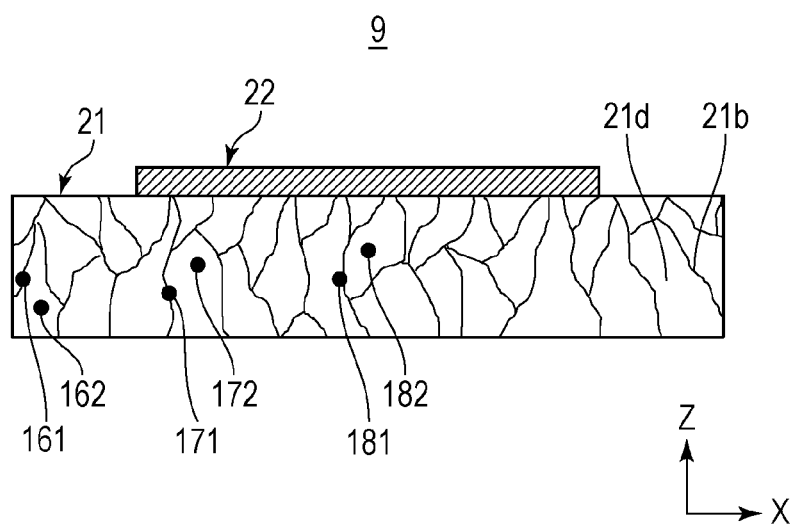

The target 9 illustrated in FIG. 4B is the same as the form illustrated in FIG. 4A in that crystal grains 21d and grain boundaries 21b are distributed in the substrate thickness direction and the substrate plane direction, but differs in that the grain boundaries 21b have the electroconductive property based on the sp2 bonding. The sp2 bonding is carbon double bonding composed of σ bonding and π bonding.

There are a plurality of carbon allotropes that differs in concentration of the sp2 bonding between diamond and graphite. Examples of these allotropes include diamond, diamond-like carbon, amorphous carbon, graphite-like carbon, and graphite. These monolayer allotropes contain π electron conjugated system double bond in accordance with the concentration of the sp2 bonding, and the electroconductive tendency is determined.

In the present invention, the electroconductive property of the transmissive substrate 21 is evaluated using the concentration of the conducting path (π electron conjugated system double bond) based on the sp2 bonding as an index. More specifically, the evaluation uses a full width at half maximum of Raman scattering peak in wavenumber 1,580 $cm^{-1}$ called G peak. In the present specification, the Raman scattering peak is hereinafter referred to as Raman shift. As the full width at half maximum of the Raman shift in wavenumber 1,580 $cm^{-1}$ reduces, the utilization of the development of networking of the conducting path relating to the sp2 bonding increases.

When the grain boundaries in which the full width at half maximum of the Raman shift in wavenumber 1,580 $cm^{-1}$ exhibits 200 $cm^{-1}$ or less are included, it is determined that the transmissive substrate includes the conducting path based on the sp2 bonding. When the grain boundaries in which the full width at half maximum of the Raman shift in wavenumber 1,580 $cm^{-1}$ exhibits 120 $cm^{-1}$ or less are included, the conducting path relating to the π-conjugated system electron trajectory is further developed, and such a conducting path defines the electrical potential of the target layer in the current field.

Next, the electrical conductivity used as the index for the conducting path of the transmissive substrate 21 is described. If a crack having a gap on the order of μm occurs in the connection electrode 47 or the target layer 22, a potential drop in the crack can be suppressed to the order of a few volts by setting the electrical conductivity of the transmissive substrate 21 at 10 $\mu Sm^{-1}$ or more. If a crack having a gap on the order of 10 μm occurs, a potential drop in the crack can be suppressed to the order of a few volts by setting the electrical conductivity of the transmissive substrate 21 at 100 $\mu Sm^{-1}$ or more, and thus discharge in the crack portion can be further suppressed. As illustrated in FIG. 4B, when the transmissive substrate 21 has an external shape larger than each of the crystal grains 21d in both the substrate thickness direction and the substrate plane direction, the grain boundaries 21b function as the conducting path in both substrate thickness direction and the substrate plane direction in an equivalent manner. Accordingly, when the size of the transmissive substrate is sufficiently larger than the crystal grain size, as illustrated in FIG. 4B, measurement of the electrical conductivity can be represented by a result of measuring the electrical conductivity in either one of the substrate thickness direction and the substrate plane direction on the assumption that there is no anisotropy.

The transmissive substrate 21, which contains the sp2 bonding in grain boundaries, is obtainable by heating the polycrystalline diamond member under a reducing atmosphere or a reduced-pressure atmosphere. For example, it can be obtained by heating the polycrystalline diamond member placed inside a vacuum chamber purged with hydrogen gas diluted with inert gas then exhausted and annealed at on the order of 800° C. to 1,600° C. for 10 minutes to 60 minutes. The upper limit of the heating condition is set in consideration of the condition where the crystal grains are not graphitized and the grain boundaries are selectively graphitized.

The transmissive substrate 21 may selectively contain the sp2 bonding in the grain boundaries in terms of thermal conductivity. If heating is performed excessively, the sp2 bonding may also be predominantly contained in the crystal grains, and the heat dissipation of the transmissive substrate may decrease. Accordingly, heating for converting the sp3 bonding to sp2 bonding may be performed in a range where the thermal conductivity of the transmissive substrate 21 is 1,000 W/(mK) or more. Specifically, a heating condition of 1,700° C. or less under a reducing atmosphere or a reduced-pressure atmosphere may be preferable, and a heating condition of 1,350° C. or less may be further preferable.

By setting the film thickness of the connection electrode 47 at 100 nm to 200 μm, connection failure of a connecting portion with the target layer 22 or the transmissive substrate 21 can be suppressed.

The electron-beam backscattering diffraction method makes use of the fact that electron beams emitted to a subject made of a crystalline material and backscattered from the subject exhibits an EBSD pattern and the fact that the EBSD pattern contains information about the crystal form and crystal orientation. The EBSD pattern is also called Kikuchi diffraction pattern. With the electron-beam backscattering diffraction method, the information about the crystal form and crystal orientation in a minute region can be obtained by scanning the subject with irradiation of electron beams and measuring and analyzing the EBSD pattern, in combination with a scanning electron microscope (SEM).

The technique for identifying distribution of crystal grains is not limited to the foregoing electron-beam backscattering diffraction method. Methods (1) to (4) described below are also applicable.

(1) With a Nomarski microscope, (2) with a scanning electron microscope (SEM), minute irregularities existing between the crystal grains are observed using secondary electron images. (3) The grain boundaries are detected by making use of microscopic cathode luminescence images and the fact that the luminescence intensity in the vicinity of the grain boundaries is low. (4) A slice subject processed by a focused ion beam (FIB) in parallel with an observation surface is prepared, the crystal grains are emphasized in annular bright-field images by a transmission electron microscope (TEM), and the distribution is identified by using image contrast.

Exemplary Embodiment 1

FIG. 1A illustrates a configuration of the target 9 produced in the present exemplary embodiment. First, two disk-shaped polycrystalline diamond members 117 each having a diameter of 5 mm and a thickness of 1 mm are prepared. The polycrystalline diamond members 117 are self-supported polycrystalline diamond produced by the CVD method. Next, residual organic compounds on the surface of each of the polycrystalline diamond members 117 are cleaned by a UV ozone ashing apparatus.

One of the polycrystalline diamond members 117 is polished, and a cross section that passes through the centers of the opposite surfaces of 5 mm in diameter is obtained by polishing. The obtained polished surface is cleaned by the UV ozone ashing apparatus, and the cleaned cross-sectional subject of the polycrystalline diamond member 117 is obtained.

This cross-sectional subject of the polycrystalline diamond member 117 is analyzed by the electron-beam backscattering diffraction method. The result is that it exhibits a polycrystalline structure in which the grain boundaries extend in the substrate thickness direction (Z direction) and the substrate plane direction (X direction), illustrated in FIG. 4A.

Next, a plurality of evaluation points for obtaining Raman spectra of the polycrystalline diamond member are set as illustrated in FIG. 4A. The evaluation points 131, 141, and 151 (also referred as "region" 131, 141 and 151) for evaluating the grain boundaries of the crystal grains, and the evaluation points 132, 142, and 152 (also referred as "region" 132, 142 and 152) for evaluating the insides of the crystal grains are set along a direction from the peripheral edge toward the center in the direction of the diameter of the polycrystalline diamond member 117. The evaluation points 131 and 132 lie in a region spaced apart by approximately 0.3 mm from the peripheral edge in the direction toward the center. Similarly, the evaluation points 141 and 142 lie in a region spaced apart by approximately 1.3 mm from the peripheral edge in the direction toward the center. The evaluation points 151 and 152 lie in a region spaced apart by approximately 2.3 mm from the peripheral edge in the direction toward the center.

Figure 5A:
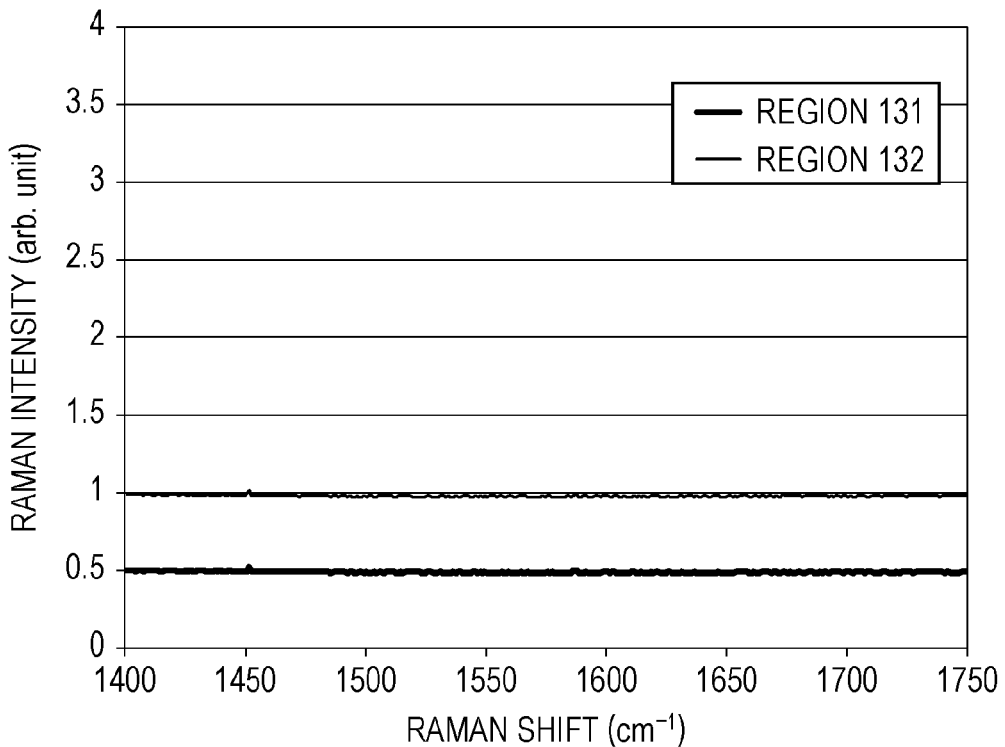
FIGS. 5A and 5B illustrate Raman spectra of polycrystalline diamond before and after graphitizing, respectively.

FIG. 5A illustrates Raman spectra at the evaluation points 131 and 132. The Raman spectra at the evaluation points 131 and 132 illustrated in FIG. 5A reveal that, in both cases, the sp3 bonding is predominantly contained and the sp2 bonding, which contributes to the electroconductive property, is virtually not contained in regions 131 and 132. The other evaluation points 141, 142, 151, and 152 exhibit Raman spectra in which the sp2 bonding, which contributes to the electroconductive property, is not virtually contained, like the evaluation points 131 and 132.

Next, the other one of the polycrystalline diamond members 117 is prepared as a precursor of the transmissive substrate 21. This polycrystalline diamond member 117 is heated under a reducing atmosphere and a reduced-pressure atmosphere in which the full pressure is 1.1E-6 Pa and the partial pressure of hydrogen is 1E-6 Pa at 1,200° C. for 60 minutes. The hydrogen is a reducing gas introduced to suppress unnecessary oxidation other than the change in the crystal structure of the polycrystalline diamond during that heating.

Next, the target layer 22 made of tungsten is deposited on one surface of the transmissive substrate 21 by using an argon gas as a carrier gas and using a tungsten sintered product as a sputter target such that the target layer 22 has a layer thickness of 6 μm, and the target 9 is produced.

The obtained target 9 is polished and cleaned, as in the case of the polycrystalline diamond member 117, and a cross-sectional subject of the target 9 is obtained.

The cross-sectional subject of the target 9 is analyzed by the electron-beam backscattering diffraction method. The result is that it exhibits a polycrystalline structure in which the grain boundaries run (are aligned) in the substrate thickness direction (Z direction) and the substrate plane direction (X direction), illustrated in FIG. 4B.

Next, evaluation points for use in evaluation by Raman spectroscopy are also set for the cross-sectional subject of the target 9. The evaluation points 161, 171, and 181 for evaluating the grain boundaries and the evaluation points 162, 172, and 182 for evaluating the insides of the crystal grains are set along a direction from the peripheral edge portion toward the central portion. The evaluation points 161 and 162 lie in a region spaced apart by approximately 0.3 mm from the peripheral edge in the direction toward the center. Similarly, the evaluation points 171 and 172 lie in a region spaced apart by approximately 1.3 mm from the peripheral edge in the direction toward the center. The evaluation points 181 and 182 lie in a region spaced apart by approximately 2.3 mm from the peripheral edge in the direction toward the center.

Figure 5B:
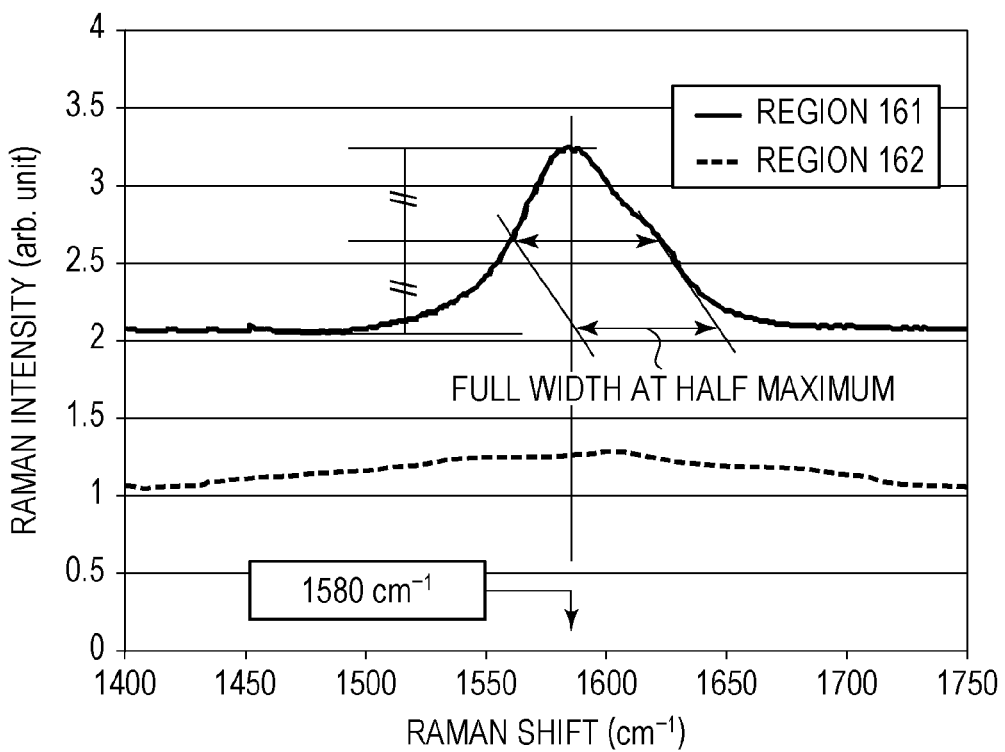

FIG. 5B illustrates Raman spectra at the evaluation points 161 and 162. The Raman spectrum at the evaluation point 161, which lies in the grain boundary, reveals that the full width at half maximum is 60.8 cm$^{-1}$ and is narrow and the sp2 bonding is predominantly contained. The Raman spectrum at the evaluation point 162, which lies inside the crystal grain, reveals that the peak intensity is ⅕ or less of that of the grain boundary and is low, the full width at half maximum is 202.3 cm$^{-1}$ and is wide, and the content of the sp2 bonding is not significant and is insufficient for expressing the electroconductive property.

The evaluation by Raman spectroscopy is performed at the other evaluation points 171, 172, 181, and 182, as in the evaluation points 161 and 162. Table 1 below lists the peak intensity and full width at half maximum of Raman shift in 1,580 cm$^{-1}$ at each of the evaluation points 161, 162, 171, 172, 181, and 182.

TABLE 1

| Evaluation Point | Position In Transmissive Substrate 21 | Peak Intensity | Full Width At Half Maximum (cm$^{-1}$) |
|---|---|---|---|
| 161 | Grain Boundary In Outer Edge Portion | 1.25 | 60.8 |
| 162 | Crystal Grain In Outer Edge Portion | 0.21 | 202.3 |
| 171 | Grain Boundary In Middle Portion | 1.24 | 63.9 |
| 172 | Crystal Grain In Middle Portion | 0.20 | 213.8 |

TABLE 1-continued

| Evaluation Point | Position In Transmissive Substrate 21 | Peak Intensity | Full Width At Half Maximum (cm$^{-1}$) |
|---|---|---|---|
| 181 | Grain Boundary In Central Portion | 1.17 | 58.9 |
| 182 | Crystal Grain In Central Portion | 0.19 | 200.1 |

Table 1 reveals that, independently of the position in the transmissive substrate 21, the peak intensity in 1,580 cm$^{-1}$ on the crystal interface (crystal boundary) is equal to or greater than 5 times that inside the crystal grain. Accordingly, it is determined that the conversion from the sp3 bonding to sp2 bonding on the grain boundaries occurs preferentially compared to that inside the crystal grains. It is also determined that the sp2 bonding, where the conducting path in the π electron conjugated system is developed, is contained over the entire area in the substrate plane direction of the transmissive substrate 21.

Exemplary Embodiment 2

Next, the polycrystalline diamond member 117 and the target 9 heated under a reducing atmosphere and a reduced-pressure atmosphere by substantially the same method as in exemplary embodiment 1 are prepared.

For the polycrystalline diamond member 117, a metal layer (not illustrated) made of tungsten and having a diameter of 3 mm and a layer thickness of 6 μm is formed on each of the opposite surfaces each having a diameter of 5 mm, as in the target layer 22 in exemplary embodiment 1, and a subject for electrical conductivity is produced. When the electrical conductivity is evaluated from the obtained electrical conductivity subject, it is 0.22 pSm$^{-1}$ at a room temperature of 300 K. The electrical conductivity is measured with a combination of Impedance Analyzer 1260 and Dielectric Interface 1296 of Solartron.

Next, for the target 9, a metal layer (not illustrated) made of tungsten and having a diameter of 3 mm and a layer thickness of 6 μm is formed on a surface opposed to the target layer 22 and having a diameter of 5 mm, as in the target layer 22, and a subject for electrical conductivity is produced. When the electrical conductivity is evaluated from the obtained electrical conductivity subject, it is 13 μSm$^{-1}$ at a room temperature of 300 K.

Exemplary Embodiment 3

Next, an X-ray generator including the target of the present invention is produced by the process described below, the X-ray generator is made to operate, and the withstand discharge performance, the intensity of outputting X-rays, and the stability of the anode current are evaluated.

The target 9 illustrated in FIGS. 1A and 1B is produced by substantially the same method as in exemplary embodiment 1. Next, the connection electrode 47 is formed in a region between the peripheral edge of the target layer 22 and a side surface of the transmissive substrate 21, and the wax material 48 made of an alloy of tin and silver is arranged on the side surface of the transmissive substrate 21. In addition, the target 9 including the connection electrode 47 and the tubular anode member 42 are bonded together with the wax material 48, and the anode 52 is produced. The anode 52 is the one in which the peripheral edge of the target 9 and the tubular inner surface of the tubular anode member 42 are annularly connected to each other, as illustrated in FIGS. 1A and 1B.

The X-ray generating tube 102 illustrated in FIG. 2A is produced by using the anode 52 in the present exemplary embodiment. When a static withstand voltage of the X-ray generating tube 102 is tested, a tube voltage of 150 kV is maintained for consecutive 10 minutes without discharge. The static withstand voltage test on the X-ray generating tube in the present exemplary embodiment is evaluation of a discharge withstand voltage by applying the tube voltage between the anode 52 and the cathode 51 without causing the electron emission source 3 in the X-ray generating tube 102 to emit the electron beam flux 5.

Next, the driving circuit 103 including a tube voltage outputting portion configured to output the tube voltage to the cathode 51 and the anode 52 is connected to the X-ray generating tube 102, they are accommodated in the remaining space 43 in the container 120, and the X-ray generator 101 illustrated in FIG. 2B is produced.

Figure 6:
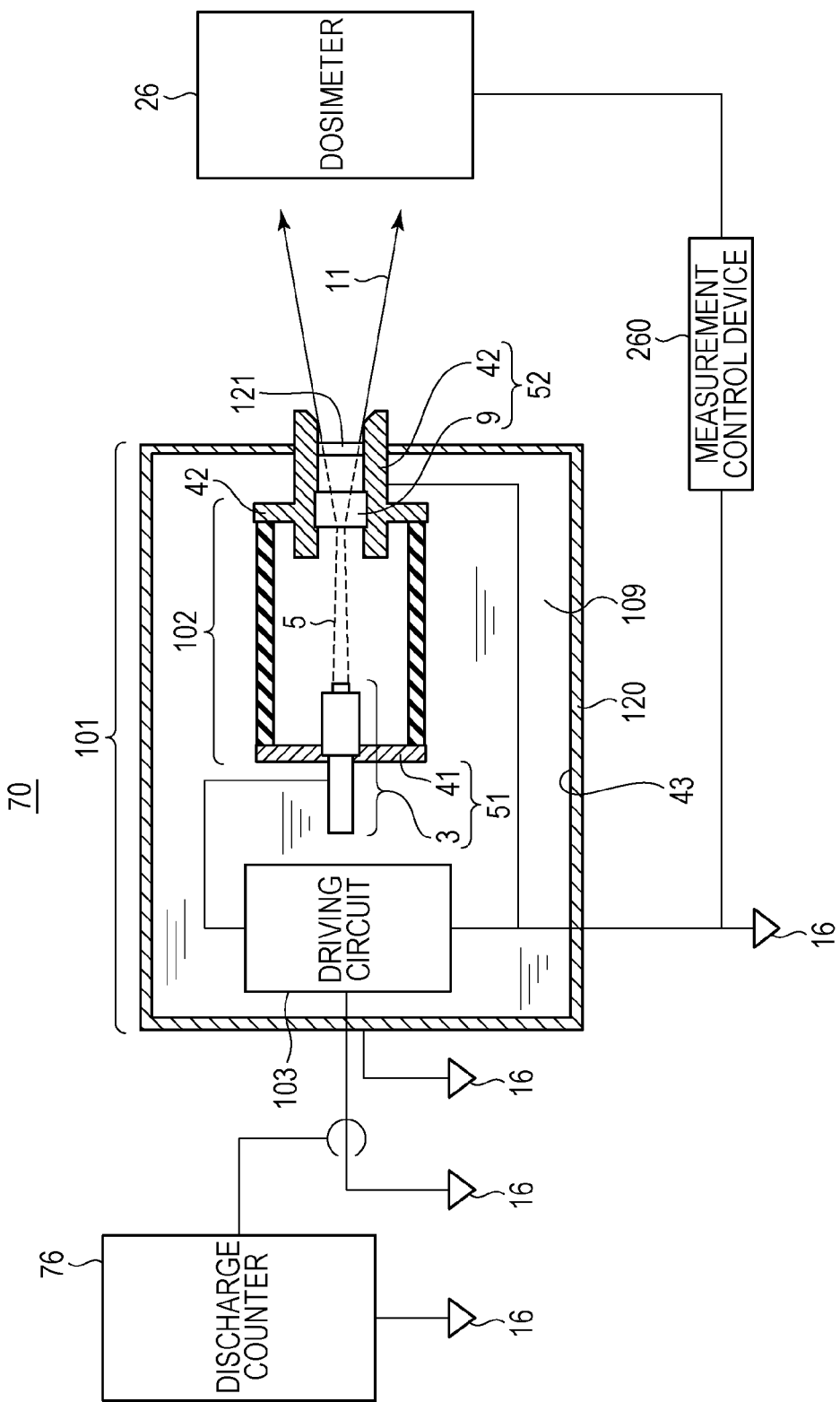
FIG. 6 is a schematic diagram that illustrates an embodiment of an evaluation system that evaluates driving stability in the X-ray generator according to the present invention.

Next, an evaluation system 70 illustrated in FIG. 6 is prepared to evaluate the withstand discharge performance and the stability of the anode current in the X-ray generator 101. The evaluation system 70 includes a dosimeter 26 in a location spaced apart by 1 m in front of the X-ray transmission window 121 in the X-ray generator 101. The dosimeter 26 is connected to the driving circuit 103 through a measurement control device 260 and is thus able to measure the intensity of outputting radiation in the X-ray generator 101.

The condition for driving the X-ray generator 101 in the present exemplary embodiment is a pulse driving in which the tube voltage of the X-ray generating tube 102 is +110 kV, the current density of electron beams emitted to the target layer 22 is 20 mA/mm$^2$, and the pulse is a repetition of 3 seconds of irradiation of electrons and 57 seconds of non-irradiation. A tube current flowing from the target layer 22 to ground electrodes 16 is measured as the anode current, and a mean value for one minute at the center in the pulse width period of the irradiation of electron beams is used. The rise time and drop time of the irradiation of electron beams are both 0.1 seconds.

The stability of the anode current is evaluated by using a retaining ratio in which an anode current after 10 hours since the start of outputting X-rays is normalized by an initial anode current. The X-ray generating tube 102 in the present exemplary embodiment is anode-grounded.

In the evaluation of the stability of the anode current, a gate current flowing between the electron emitting portion 2 and a gate electrode (not illustrated) is stabilized such that its fluctuations are made to fall within 1% by a negative feedback circuit (not illustrated).

In a test for withstand discharge performance, a state where the X-ray generator 101 is stably driven without discharge is checked by a discharge counter 76 during the evaluation of the stability of the anode current in the X-ray generator 101.

The retaining ratio of the anode current in the X-ray generator 101 in the present exemplary embodiment is 0.99. For the X-ray generator 101 including the target 9 according to the present exemplary embodiment, notable fluctuations in outputting X-rays are not observed after 1,000 exposing operations, and it is determined that a stable intensity of outputting X-rays is obtainable. When the X-ray generator 101 is disassembled after the evaluation of the stability of the anode current and the anode 52 is extracted, a crack 47c having a gap of 2 µm is found in the connection electrode 47, as illustrated in FIG. 1C, but traces of discharge are not recognized in the anode 52.

In FIG. 1C, for the sake of understanding, the grain boundaries 21b and crystal grains 21d predominantly containing the sp2 bonding are illustrated in the transmissive substrate 21. The grain boundaries 21b are the conducting path arranged electrically in parallel with the connection electrode 47, and the electrical potential of the target layer 22 is estimated to be defined in the current field.

Exemplary Embodiment 4

Figure 3:
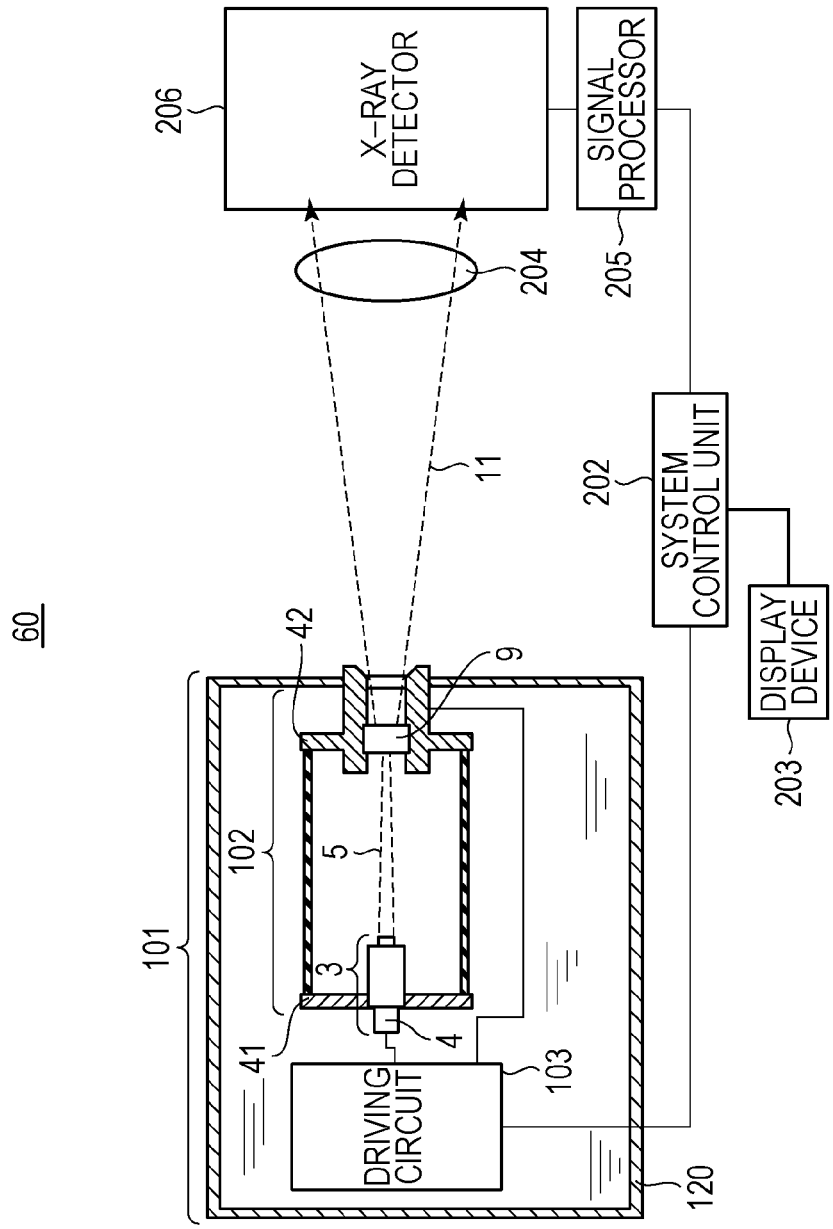
FIG. 3 is a schematic diagram that illustrates an embodiment of a radiography system that includes the transmission-type target according to the present invention.

In the present exemplary embodiment, the radiography system 60 illustrated in FIG. 3 is produced by using the X-ray generator 101 described in exemplary embodiment 3.

The radiography system 60 can provide X-ray photographed images whose photographed qualities do not vary among the images and whose signal-to-noise ratios are high by including the X-ray generator 101, in which discharged is suppressed and the fluctuations in anode current are reduced.

Exemplary Embodiment 5

The X-ray generating tube 102 illustrated in FIG. 2A and the X-ray generator 101 illustrated in FIG. 2B are produced by substantially the same method as in exemplary embodiment 3, except for not producing the connection electrode 47. For the obtained X-ray generator 101, the withstand discharge performance, the intensity of outputting X-rays, and the stability of the anode current are evaluated, as in exemplary embodiment 3.

The retaining ratio of the anode current in the X-ray generator 101 in the present exemplary embodiment is 0.97. For the X-ray generator 101 including the target 9 according to the present exemplary embodiment, notable fluctuations in outputting X-rays are not observed after 1,000 exposing operations, and it is determined that a stable intensity of outputting X-rays is obtainable. When the X-ray generator 101 is disassembled after the evaluation of the stability of the anode current and the anode 52 is extracted, traces of discharge are not recognized in the anode 52. The electrical potential of the target layer in the target in the present exemplary embodiment is estimated to be defined in the current field by the transmissive substrate.

The electroconductive property of the polycrystalline diamond can also be expressed by introducing a dopant metal. For the polycrystalline diamond in which the electroconductive property expressed by the dopant metal is predominant, the electroconductive property may be changed by diffusion movement of the dopant metal under a high-temperature environment, and the electrical potential of the target layer may not be stably defined. In contrast, for the polycrystalline diamond in which the electroconductive property expressed by the grain boundaries 21b having the sp2 bonding is predominant, as in the transmission-type target 9 described in the above-described exemplary embodiments 1 to 5, the thermally stable conducting path is obtainable.

The present invention can provide the X-ray generating tube having reliable anode connection, by suppressing electrical connection failure between the target layer and the anode member, and thereby achieving stable output of X-rays, and suppressing parasitical electric discharge. The reliable X-ray generator and radiography system including the X-ray generating tube in the present invention can also be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-145922, filed Jul. 16, 2014, which is hereby incorporated by reference herein in its entirety.

What is claimed is:

1. A transmission-type target comprising:
   a target layer configured to generate X-rays in response to irradiation of electrons; and
   a transmissive substrate supporting the target layer and configured to allow the X-rays generated in the target layer to pass therethrough,
   wherein the transmissive substrate includes polycrystalline diamond in which grain boundaries extend in a substrate thickness direction and a substrate plane direction, and the grain boundaries define an electrical potential of the target layer.

2. The transmission-type target according to claim 1, wherein the grain boundaries define the electrical potential of the target layer in a current field.

3. The transmission-type target according to claim 1, wherein the grain boundaries include sp2 bonding.

4. The transmission-type target according to claim 1, wherein the grain boundaries exhibit a Raman scattering peak centered in wavenumber 1,580 $cm^{-1}$.

5. The transmission-type target according to claim 4, wherein a full width at half maximum of the Raman scattering peak is equal to or smaller than 200 $cm^{-1}$.

6. The transmission-type target according to claim 5, wherein the full width at half maximum of the Raman scattering peak is equal to or smaller than 120 $cm^{-1}$.

7. The transmission-type target according to claim 4, wherein the full width at half maximum of the Raman scattering peak centered in wavenumber 1,580 $cm^{-1}$ for the grain boundaries is smaller than that for inside the crystal grains.

8. The transmission-type target according to claim 4, wherein a peak intensity of the Raman scattering peak centered in wavenumber 1,580 $cm^{-1}$ for the grain boundaries is higher than that for inside the crystal grains.

9. The transmission-type target according to claim 8, wherein the intensity of the Raman scattering peak centered in wavenumber 1,580 $cm^{-1}$ for the grain boundaries is equal to or greater than 5 times that for inside the crystal grains.

10. The transmission-type target according to claim 4, wherein the crystal grains do not significantly have the Raman scattering peak in wavenumber 1,580 $cm^{-1}$.

11. The transmission-type target according to claim 1, wherein the transmissive substrate has thermal conductivity equal to or greater than 1,000 W/(mK).

12. The transmission-type target according to claim 1, wherein the transmissive substrate has electrical conductivity equal to or greater than 10 $\mu Sm^{-1}$.

13. An X-ray generating tube comprising:
   an anode including the transmission-type target according to claim 1 and an anode member electrically connected to the transmissive substrate on a peripheral edge of the transmissive substrate;

a cathode including an electron emission source configured to irradiate the target layer with electrons and a cathode member electrically connected to the electron emission source; and an insulating tube connected to the anode member and the cathode member.

14. An X-ray generator comprising:
the X-ray generating tube according to claim 13; and
a driving circuit configured to apply a tube voltage between the anode and the cathode.

15. A radiography system comprising:
the X-ray generator according to claim 14;
an X-ray detector configured to detect an X ray emitted from the X-ray generator and passing through a subject; and
a system control unit configured to integrally control the X-ray generator and the X-ray detector.

16. The transmission-type target according to claim 1, wherein the transmissive substrate has an electrical conductivity in the grain boundaries sufficient to define the electrical potential of the target layer via the grain boundaries.

17. The transmissive-type target according to claim 16, wherein the transmissive substrate has electrical conductivity equal to or greater than 10 $\mu Sm^{-1}$.

18. A transmission-type target comprising:
a target layer configured to generate X-rays in response to irradiation of electrons; and
a transmissive substrate supporting the target layer and configured to allow the X-rays generated in the target layer to pass therethrough,
wherein the transmissive substrate includes polycrystalline diamond in which grain boundaries extend in a substrate thickness direction and a substrate plane direction, and the grain boundaries include sp2 bonding, and
wherein the grain boundaries define an electrical potential of the target layer in a current field.

19. The transmission-type target according to claim 18, wherein the grain boundaries exhibit a Raman scattering peak whose full width at half maximum is equal to or smaller than 200 $cm^{-1}$ centered in wavenumber 1,580 $cm^{-1}$.

20. A transmissive-type target comprising:
a target layer configured to generate X-rays in response to irradiation of electrons; and
a transmissive substrate supporting the target layer and configured to allow the X-rays generated in the target layer to pass therethrough,
wherein the transmissive substrate includes a plurality of crystal grains and grain boundaries between the crystal grains including sp3 bonding, and the grain boundaries define an electrical potential of the target layer in a current field.

21. The transmissive-type target according to claim 20, wherein the grain boundaries include sp2 bonding.

22. The transmissive-type target according to claim 20, wherein the grain boundaries exhibit a Raman scattering peak centered in wavenumber 1,580 $cm^{-1}$.

23. The transmissive-type target according to claim 22, wherein a full width at half maximum of the Raman scattering peak is equal to or smaller than 200 $cm^{-1}$.

24. The transmissive-type target according to claim 23, wherein the full width at half maximum of the Raman scattering peak is equal to or smaller than 120 $cm^{-1}$.

25. The transmissive-type target according to claim 23, wherein the full width at half maximum of the Raman scattering peak centered in wavenumber 1,580 $cm^{-1}$ for the grain boundaries is smaller than that for inside the crystal grains.

26. The transmissive-type target according to claim 22, wherein a peak intensity of the Raman scattering peak centered in wavenumber 1,580 $cm^{-1}$ for the grain boundaries is higher than that for inside the crystal grains.

27. The transmissive-type target according to claim 26, wherein the intensity of the Raman scattering peak centered in wavenumber 1,580 $cm^{-1}$ for the grain boundaries is equal to or greater than 5 times that for inside the crystal grains.

28. The transmissive-type target according to claim 20, wherein the crystal grains do not significantly have a Raman scattering peak in wavenumber 1,580 $cm^{-1}$.

29. The transmissive-type target according to claim 20, wherein the transmissive substrate has thermal conductivity equal to or greater than 1,000 W/(mK).

30. The transmissive-type target according to claim 20, wherein the transmissive substrate has electrical conductivity equal to or greater than 10 $\mu Sm^{-1}$.

31. The transmissive-type target according to claim 20, wherein the substrate includes a polycrystalline diamond, and
wherein the grain boundaries and the crystal grains are included in the polycrystalline diamond.

32. The transmissive type target according to claim 20, wherein the grain boundaries extend in a substrate thickness direction and a substrate plane direction.

33. An X-ray generating tube comprising:
an anode including the transmissive-type target according to claim 20 and an anode member electrically connected to the transmissive substrate on a peripheral edge of the transmissive substrate;
a cathode including an electron emission source configured to irradiate the target layer with electrons and a cathode member electrically connected to the electron emission source; and
an insulating tube connected to the anode member and the cathode member.

34. An X-ray generator comprising:
the X-ray generating tube according to claim 33; and
a driving circuit configured to apply a tube voltage between the anode and the cathode.

35. A radiography system comprising:
the X-ray generator according to claim 34;
an X-ray detector configured to detect an X ray emitted from the X-ray generator and passing through a subject; and
a system control unit configured to integrally control the X-ray generator and the X-ray detector.

36. A transmission-type target comprising:
a target layer configured to generate X-rays in response to irradiation of electrons; and
a transmissive substrate supporting the target layer and configured to allow the X-rays generated in the target layer to pass therethrough,
wherein the transmissive substrate includes polycrystalline diamond in which grain boundaries extend in a substrate thickness direction and a substrate plane direction, and the grain boundaries include sp2 bonding, and
wherein the grain boundaries have a crystallinity in a sp2 bonding enough to define an electrical potential of the target layer.

37. A transmission-type target comprising:
a target layer configured to generate X-rays in response to irradiation of electrons; and a transmissive substrate supporting the target layer and configured to allow the X-rays generated in the target layer to pass therethrough, wherein the transmissive substrate includes polycrystalline diamond in which grain boundaries extend in a substrate thickness direction and a substrate plane direction, and the grain boundaries include sp2 bonding, and wherein the transmissive substrate has an electrical conductivity in the grain boundaries sufficient to define the electrical potential of the target layer via the grain boundaries.

38. The transmissive-type target according to claim 37, wherein the transmissive substrate has electrical conductivity equal to or greater than $10 \, \mu Sm^{-1}$.

39. A transmissive-type target comprising:

a target layer configured to generate X-rays in response to irradiation of electrons; and a transmissive substrate supporting the target layer and configured to allow the X-rays generated in the target layer to pass therethrough, wherein the transmissive substrate includes a plurality of crystal grains and grain boundaries between the crystal grains including sp3 bonding, and the transmissive substrate has an electrical conductivity in the grain boundaries sufficient to define the electrical potential of the target layer via the grain boundaries.

40. The transmissive-type target according to claim 39, wherein the transmissive substrate has electrical conductivity equal to or greater than $10 \, \mu Sm^{-1}$.

* * * * *